United States Patent [19]

Moran et al.

[11] Patent Number: 5,895,390
[45] Date of Patent: Apr. 20, 1999

[54] PIN PLACEMENT GUIDE USED IN MAKING A BONE ENTRY HOLE FOR IMPLANTATION OF AN INTRAMEDULLARY NAIL

[75] Inventors: Michael C. Moran, Palos Heights, Ill.; Robert Border, Bourbon, Ind.

[73] Assignee: Biomet, Inc., Warsaw, Ind.

[21] Appl. No.: 08/898,809

[22] Filed: Jul. 23, 1997

Related U.S. Application Data

[62] Division of application No. 08/716,086, Sep. 19, 1996, Pat. No. 5,741,266.

[51] Int. Cl.$^6$ ................................................ A61F 5/04
[52] U.S. Cl. ........................... 606/96; 606/80; 606/98; 606/104
[58] Field of Search ................... 606/96, 80, 48, 606/104; 408/115 R, 115 B

[56] References Cited

U.S. PATENT DOCUMENTS

| | | |
|---|---|---|
| 2,181,746 | 11/1939 | Siebrandt . |
| 2,200,120 | 5/1940 | Nauth . |
| 2,547,571 | 4/1951 | Ettinger . |
| 2,607,339 | 8/1952 | Price . |
| 2,697,433 | 12/1954 | Zehnder . |
| 3,086,408 | 4/1963 | Donals . |
| 3,598,496 | 8/1971 | Skinner . |
| 3,626,513 | 12/1971 | Pytlak . |
| 3,708,237 | 1/1973 | Kruse . |
| 3,727,611 | 4/1973 | Schultz . |
| 4,037,592 | 7/1977 | Kronner . |
| 4,341,206 | 7/1982 | Perrett et al. . |
| 4,465,065 | 8/1984 | Gotfried . |
| 4,502,475 | 3/1985 | Weigle et al. . |
| 4,522,201 | 6/1985 | Tongue . |
| 4,599,999 | 7/1986 | Klaue . |
| 5,429,641 | 7/1995 | Gotfried . |
| 5,769,856 | 6/1998 | Dong et al. ............................ 606/96 |

FOREIGN PATENT DOCUMENTS

| | | |
|---|---|---|
| 734245 | 4/1943 | German Dem. Rep. . |
| 925328 | 5/1982 | U.S.S.R. . |
| 876125 | 10/1991 | U.S.S.R. . |

*Primary Examiner*—Michael Buiz
*Assistant Examiner*—Julian W. Woo
*Attorney, Agent, or Firm*—Michael McNeil

[57] ABSTRACT

In a method of making an entry hole for implanting a retrograde humeral nail across a fracture in a humerus comprises the initial step of providing a pin placement guide having a base with a bone contact surface and a guide portion attached to the base. A guide bore with a guide axis extends through the guide portion and the bone contact portion of the base. The pin placement guide is clamped on the humerus so that the guide axis is at a relatively small angle of less than 20° with respect to the bone axis of the humerus, and the bone contact surface is substantially aligned with the bone axis. Next, a guide pin with a tip is inserted through the guide bore. A guide hole is bored into the bone along the guide axis with the guide pin. Next, the clamp and pin placement guide are removed. Finally, the guide hole is reamed to enlarge it into an entry hole that is at an angle with respect to the bone axis equal or less than that of the guide axis. The retrograde humeral nail is then inserted through the entry hole in a conventional manner.

20 Claims, 7 Drawing Sheets

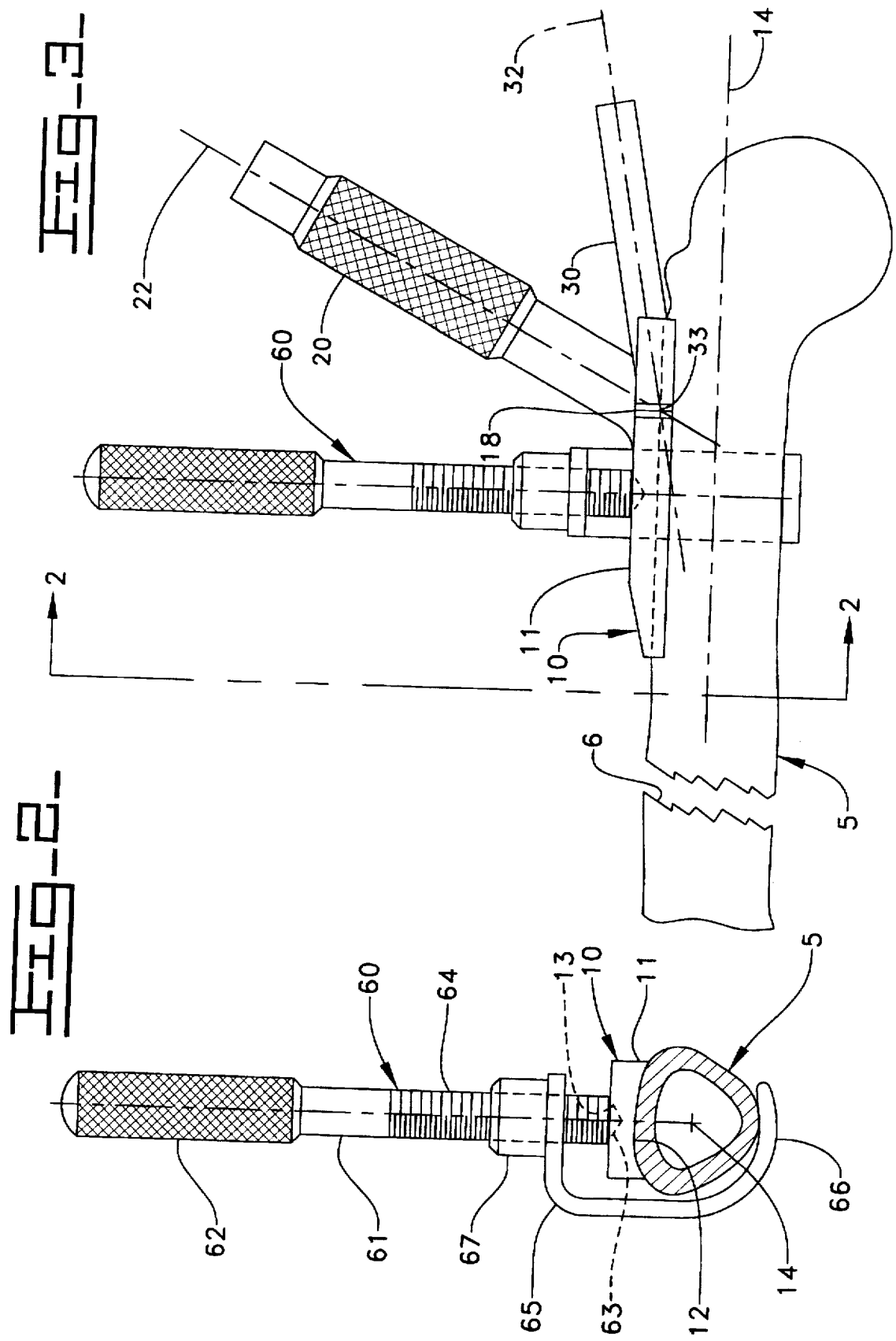

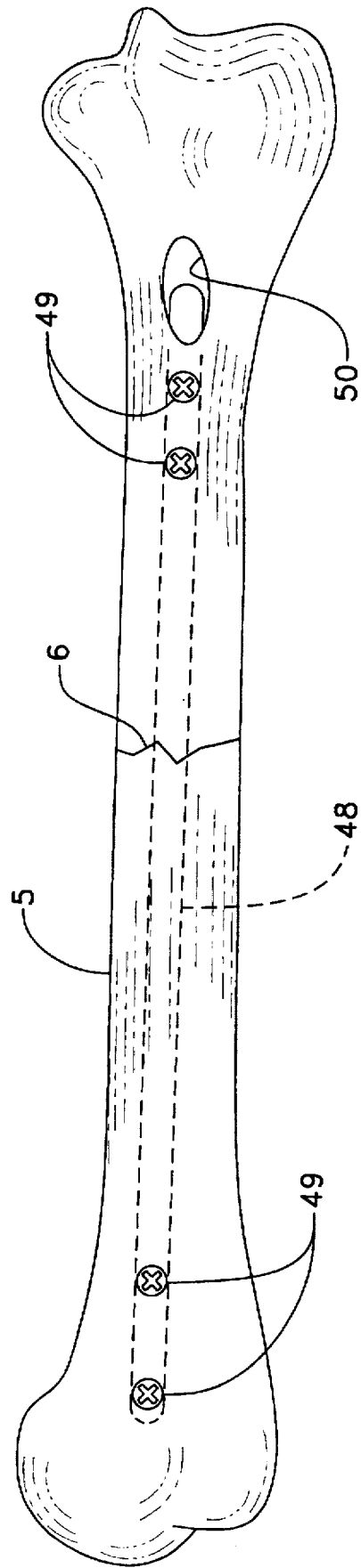

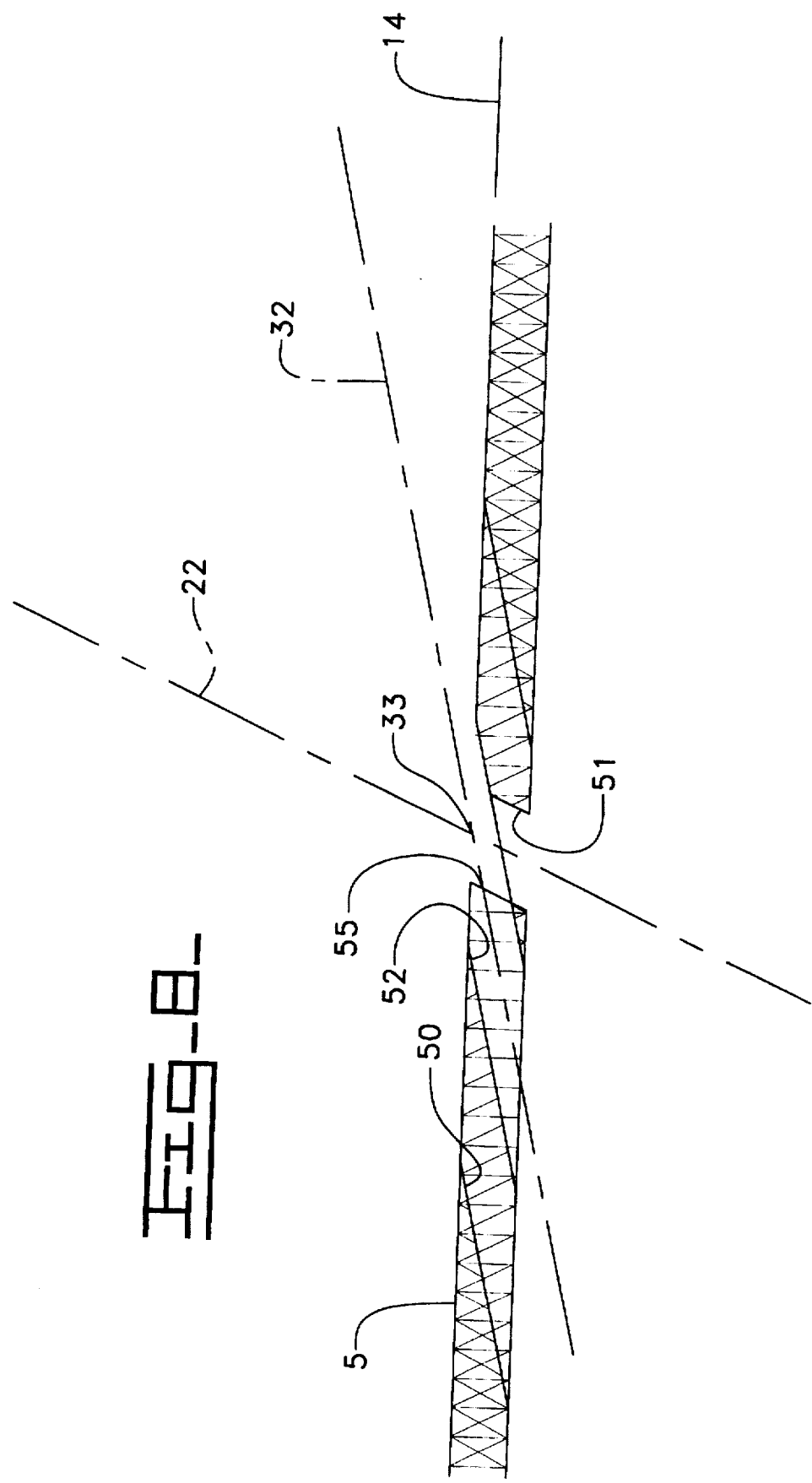

PIN PLACEMENT GUIDE USED IN MAKING A BONE ENTRY HOLE FOR IMPLANTATION OF AN INTRAMEDULLARY NAIL

RELATION TO OTHER PATENT APPLICATION

This is a divisional application of pending U.S. patent application Ser. No. 08/716,086, filed Sep. 19, 1996, entitled PIN PLACEMENT GUIDE AND METHOD OF MAKING A BONE ENTRY HOLE FOR IMPLANTATION OF AN INTRAMEDULLARY NAIL, now U.S. Pat. No. 5,741,266.

FIELD OF THE INVENTION

The present invention relates generally to a pin placement guide for use in making a bone entry hole for the implantation of an intramedullary nail across a fracture in an elongated bone, and more particularly to a pin placement guide for making an entry hole in a humerus for the implantation of a retrograde humeral nail.

BACKGROUND OF THE INVENTION

It is well known that proximal third and/or mid-shaft humeral fractures are often best mended using a retrograde humeral nailing technique in order to avoid disturbing the rotator cuff or the subacromial space. In a typical surgical technique of this type, a longitudinal incision is made through the skin and underlying tissue in order to identify and expose the olecranon fossa in the posterior humerus and the region just proximal to the olecranon fossa. In the prior art technique, a drill is then used to open the posterior humeral cortex about 2½ centimeters from the proximal— most extent of the olecranon fossa. This initial opening is generally made along an axis substantially perpendicular to the bone axis. Because the nail must enter the bone at a relatively low angle, the opening must be elongated, generally by the use of a small curved awl or a ronguer.

Unfortunately, this technique of enlarging an original pilot hole into an oblong opening to facilitate receiving the humeral nail can sometimes result in unnecessary bone damage due to the increased pressure caused by the hole enlarging device. This increased pressure may even crack the bone at the thin bone location, which can be on the order of about 1/16 of an inch in thickness. This technique is also undesirable in that it almost always inevitably leads to the removal of more bone cortex than is actually necessary to insert the retrograde humeral nail. After the entry hole is made sufficiently oblong and large to accommodate a humeral nail at a low angle, any and several known techniques can be utilized to finally implant the nail within the humerus.

The present invention is directed to overcoming problems associated with prior art methods of making an entry hole to implant an intramedullary nail across a fracture in an elongated bone, especially as it relates to an entry hole for a retrograde humeral nail.

SUMMARY OF THE INVENTION

A method of making an entry hole for implanting an intramedullary nail across a fracture in an elongated bone having a bone axis includes the initial step of providing a pin placement guide. The pin placement guide has a base with a bone contact surface and a guide portion attached to the base. A guide bore with a guide axis extends through the guide portion and the bone contact surface of the base. The pin placement guide is clamped on the elongated bone with a clamp so that the guide axis is at a relatively small angle of less than 20° with respect to the bone axis. In addition, the bone contact surface of the base is substantially aligned with the bone axis. A guide pin with a tip is then inserted through the guide bore. Next a guide hole is bored in the elongated bone along the guide axis using the guide pin. The clamp and pin placement guide are then removed from the elongated bone. Finally, the guide hole is reamed to enlarge it into an entry hole that is centered along an entry axis that is at a smaller angle than said guide axis with respect to said bone axis. The retrograde humeral nail may then be implanted using one of several accepted techniques.

One object of the present invention is to provide an improved method for making an entry hole to implant an intramedullary nail across a fracture in an elongated bone.

Another object of the present invention is to provide an improved method of implanting a retrograde humeral nail.

Still another object of the present invention is to provide an improved pin placement guide for making entry holes in an elongated bone at a shallow angle.

BRIEF DESCRIPTION OF THE DRAWINGS

FIG. 2 is a sectioned view through a bone along section lines 2—2 of FIG. 3.

FIG. 3 is a side elevational view of a pin placement guide clamped to a bone according to one aspect of the present invention.

FIG. 7 is a top elevational view of a humerus with a retrograde humeral nail implanted therein according to the present invention.

FIG. 8 is an enlarged sectioned view of a bone cortex with openings bored therein according to the present invention.

DETAILED DESCRIPTION OF THE PREFERRED EMBODIMENTS

Figure 1:
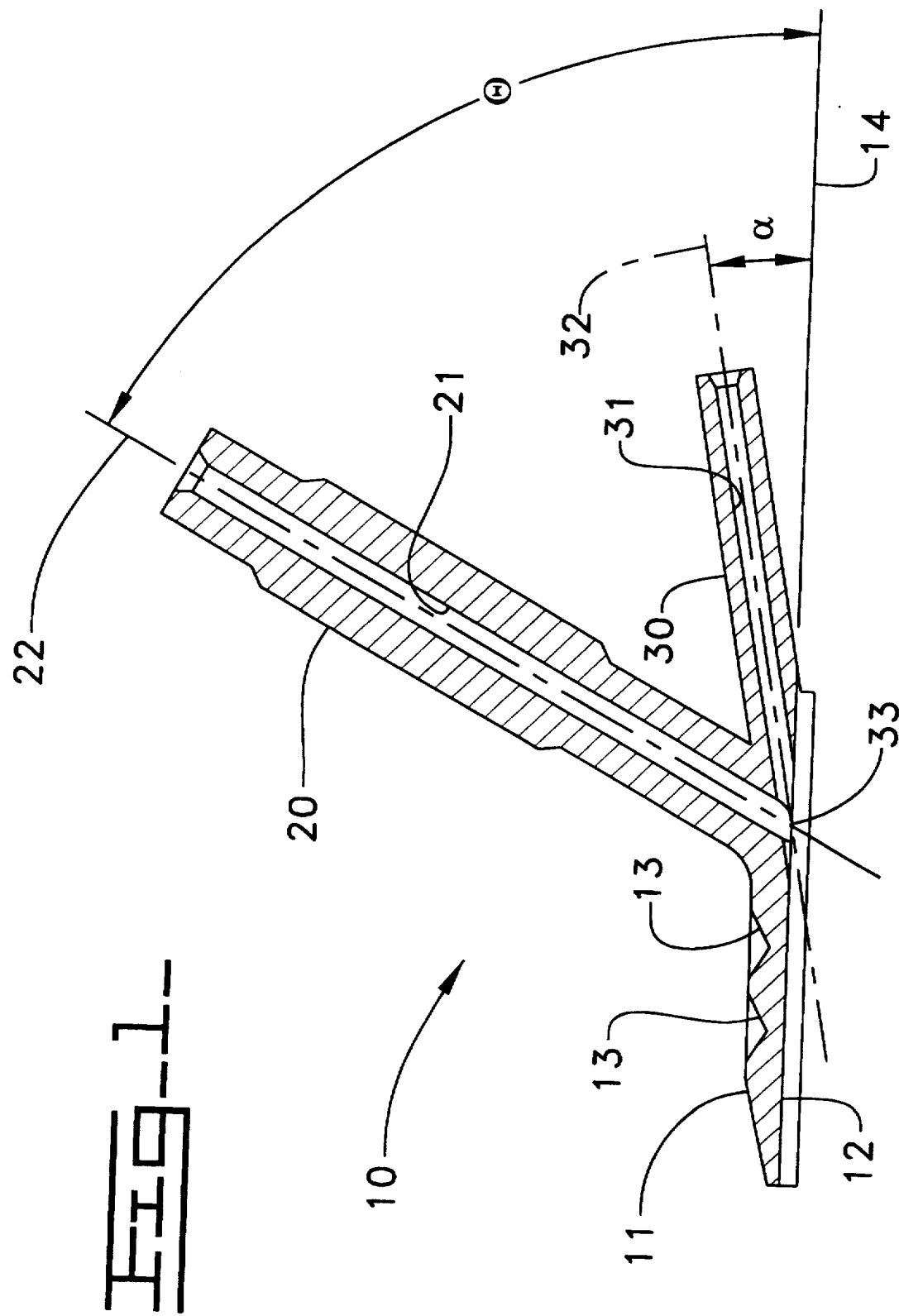
FIG. 1 is a sectioned side elevational view of a pin placement guide according to one embodiment of the present invention.
Figure 4:
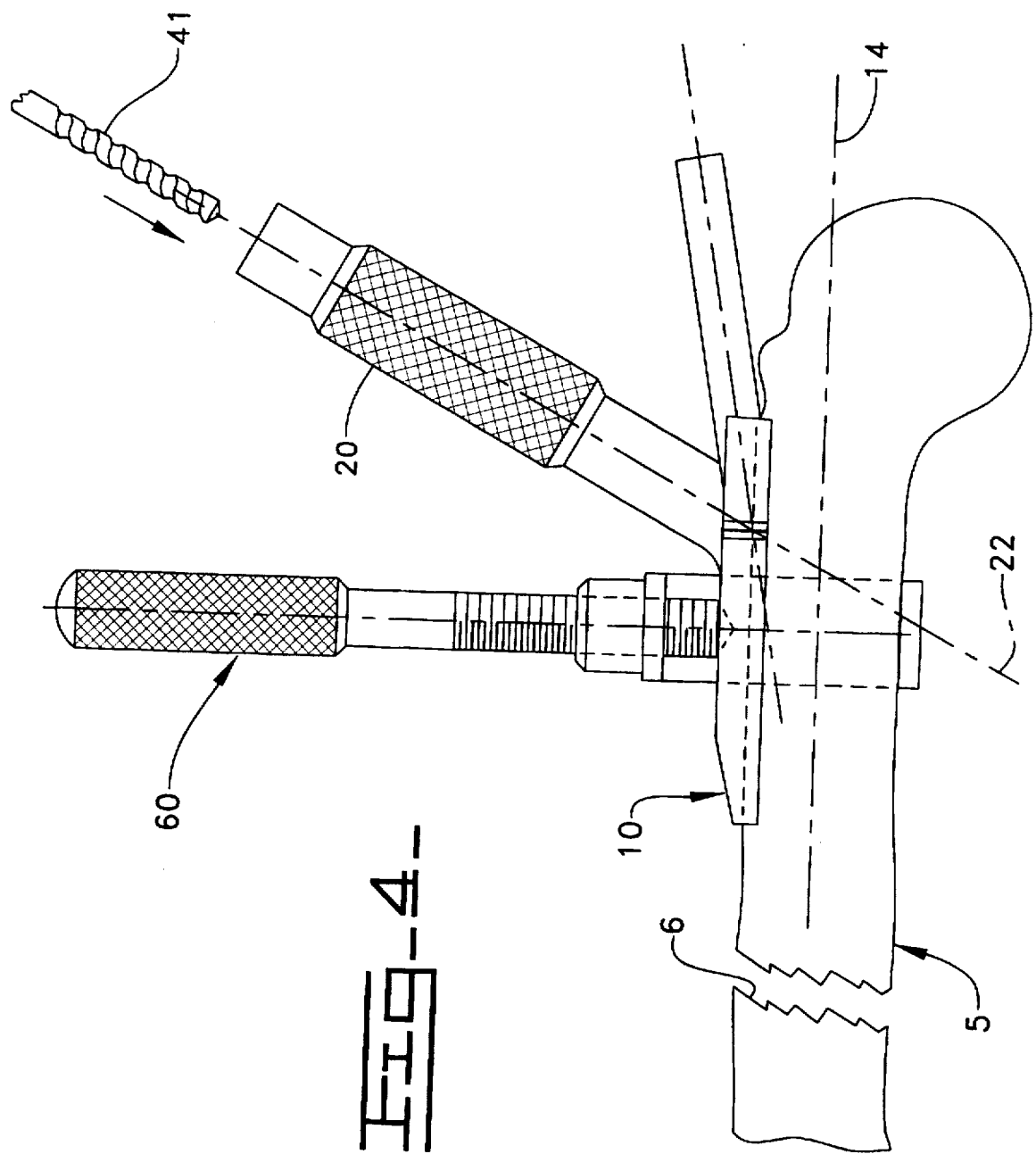
FIG. 4 is a side elevational view showing the pilot hole drilling step of the method according to the present invention.
Figure 5:
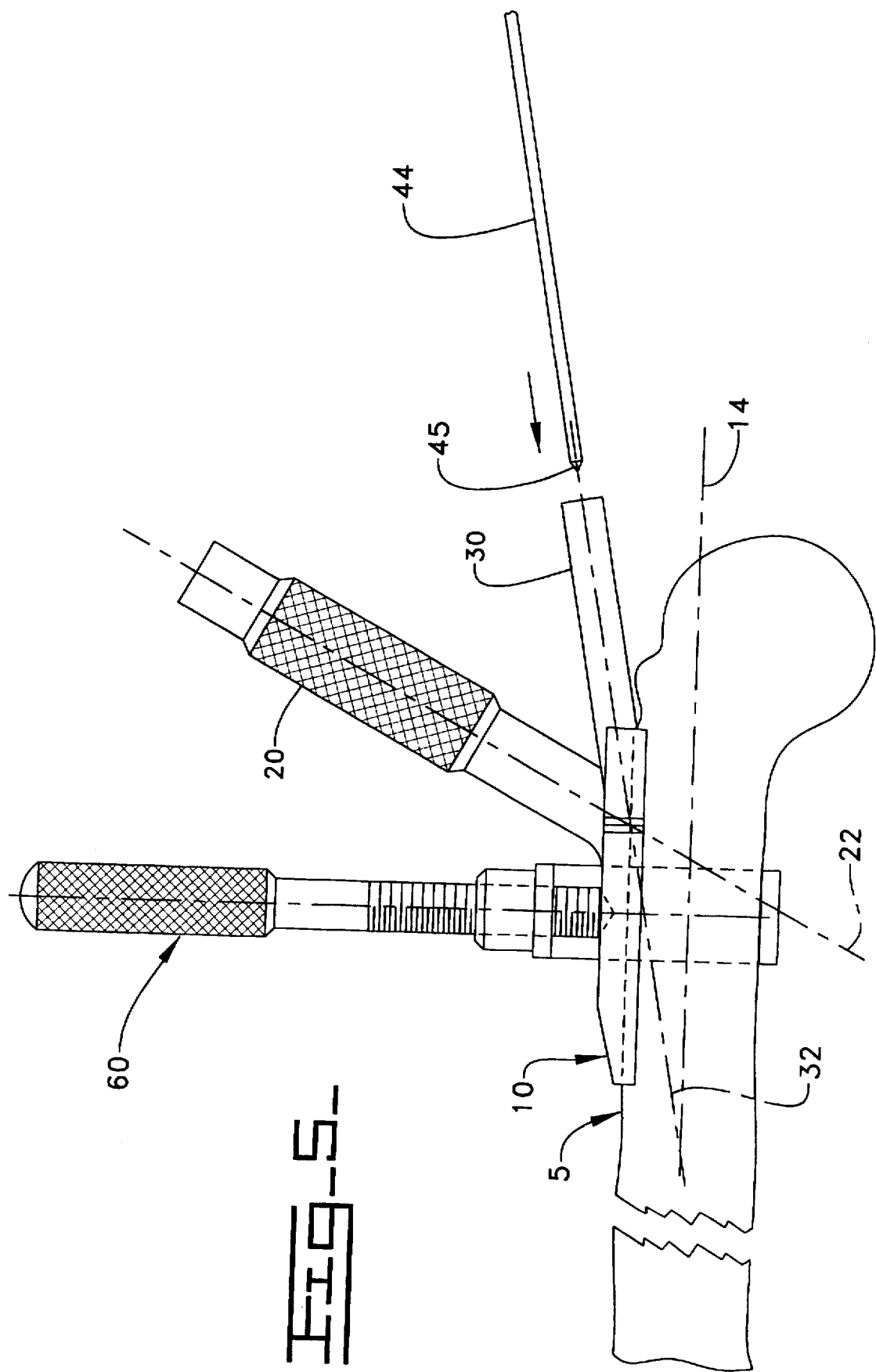
FIG. 5 is a side elevational view showing a guide hole boring step of the present invention.
Figure 6:
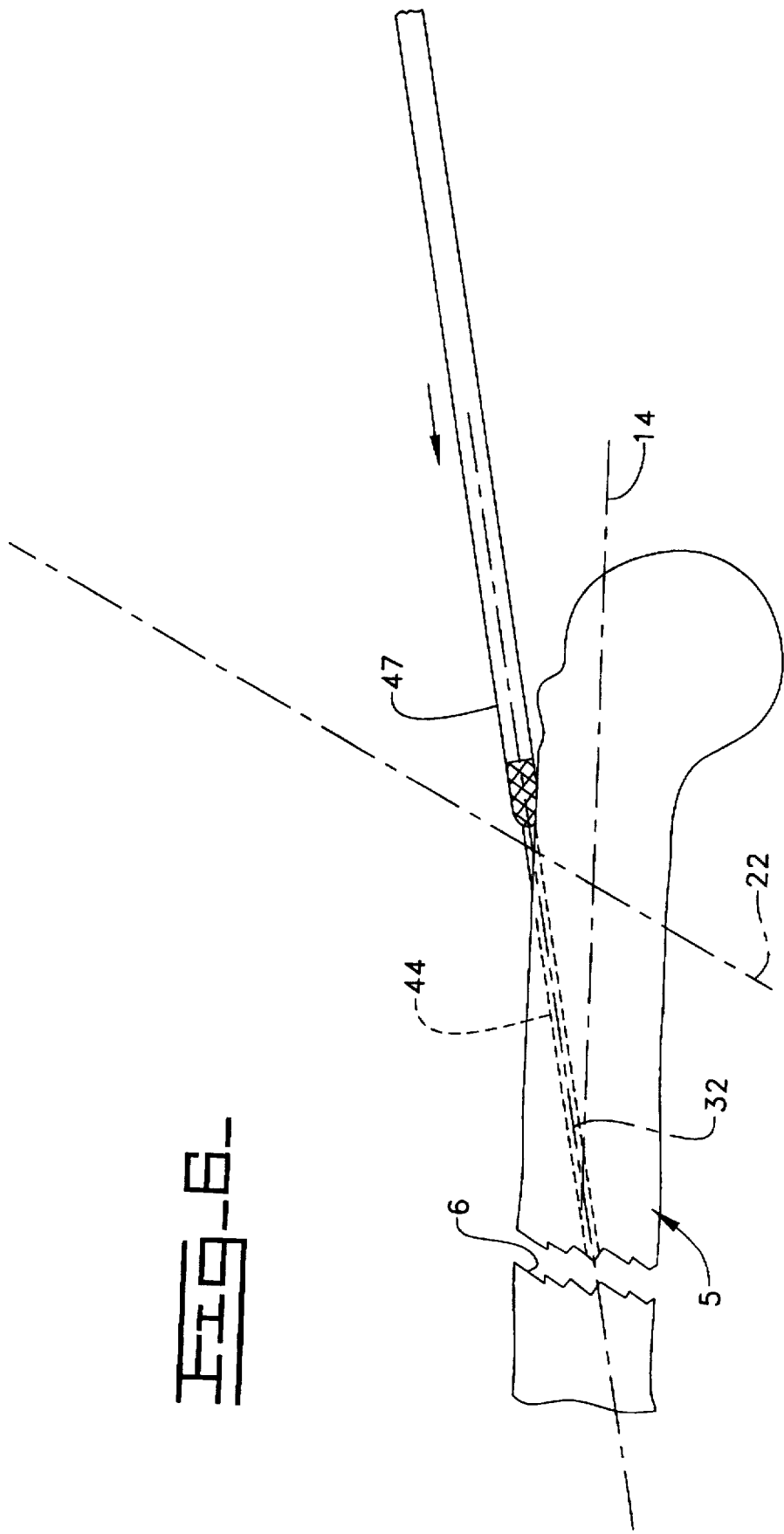
FIG. 6 is a side elevational view showing a reaming step of the present invention.

Referring now to FIG. 1, a pin placement guide 10 includes a base 11, a knurled handle 20 attached to base 11 and a guide portion 30 also attached to the base. Each of these components is preferably machined from individual pieces of a suitable surgical grade metallic alloy, and then welded to one another in the form shown. Base 11 includes an arched bone contact surface 12 that rests against the outer surface of an elongated bone, which is substantially parallel to the bone axis 14 of the bone. A pilot bore 21 extends through handle 20 and bone contact surface 12. Pilot bore 21 is aligned with a pilot axis 22 which forms an angle theta with respect to bone axis 14. Angle theta should generally be greater than about 45° and is preferably on the order of about 60°. A guide bore 31 extends through guide portion 30 and bone contact surface 12 of base 11. Guide bore 31 is aligned with a guide axis 32 which forms an angle alpha with respect to bone axis 14. Preferably, pilot axis 22, guide axis 32 and bone axis 14 are co-planer and fixed with respect to one another. Angle alpha is less than 20°, should be between about 5° and 15° and is preferably about 10°.

Referring now to FIGS. 2 and 3, pin placement guide 10 is shown clamped to a humerus 5 using a clamping device 60. Clamp 60 is of a type generally known in the art having a rod 61 with a knurled handle 62, a threaded portion 64 and a pointed end 63. A gripping portion 65 includes a threaded barrel 67 and an arm 66. Pin placement guide 10 is clamped to a bone by locating arm 66 of clamp 60 underneath the bone and then tightening rod 61 down until pointed end 63 is received in one of the indentations 13 made in the outer surface of base 11. In this case, pin placement guide 10 is shown attached adjacent the posterior end of a humerus 5 with a mid-shaft fracture 6.

A notch 18 machined in the outer surface of base 11 provides a visual cue to the health care provider as to the location of intersection point 33, which represents the intersection of pilot axis 22 with guide axis 32. This intersection point 33 is preferably adjacent bone contact surface 12 of base 11 so that the intersection point rests at about the bone's outer surface when the pin placement guide 10 is positioned as shown.

Referring now to FIGS. 4–7, the technique for making an entry hole into an elongated bone according to the present invention is illustrated in its various steps. In particular, after the pin placement guide 10 is clamped to bone 5 at the proper location near one end of the bone, a drilling device 41 is advanced through handle 20 along pilot axis 22. A pilot hole is made in bone 5 along pilot axis 22 using drilling device 41. Drilling device 41 may be of any type known in the art for boring holes into bone. Next, after drilling device 41 has been removed, a guide pin 44 having a boring tip 45 is advanced into guide portion 30 along guide axis 42. Boring tip 45 is preferably a trocar tip but could equally well be any other suitable boring tip known in the art.

By properly sizing the pilot hole, and because of the intersecting relationship between pilot axis 32 and guide axis 32, the tip 45 of guide pin 44 will eventually enter the pilot hole in bone 5. At this point, guide pin 44 is utilized in a conventional manner to bore a guide hole into bone 5 along guide axis 32. While the making of a pilot hole is not essential to the present invention, it does better facilitate the making of a guide hole at a shallow angle as shown. When no pilot hole is made, more care must be taken when boring the guide hole because of the tendency of some boring tips to skip along the outer surface of the bone at such a shallow angle.

After the guide hole is made, the clamp 60 is loosened and both pin placement guide 10 and clamp 60 are removed while leaving guide pin 44 in place. At this point, or before the pin placement guide has been removed, a blunt tipped guide rod can be inserted along guide axis 32 in place of guide pin 44. In other applications it may be desirable to simply leave guide pin 44 in place and utilize it as a guide for a cannulated reamer. In any event, it is desirable that the pin placement guide be removed before the reaming step so that the reamed entry hole's axis can be made even shallower than the angle of the guide axis.

In the next step a cannulated reamer 46 having a diameter about 1 millimeter larger than the desired nail to be utilized, is advanced over guide pin 44 along guide axis 32. The guide hole is then reamed generally along guide axis 32 to enlarge the same to the diameter of the reamer 46. However, because the guide pin can often be maneuvered or levered to a shallower angle with the pin placement guide removed, the reamed entry hole at an angle of less than about 10 degrees. The end result being an oblong entry hole 50 with a relatively minimum amount of bone removed to accommodate a nail of a particular diameter entering the bone at a shallow angle. In other words, by utilizing a reamer with a slightly larger diameter than the intended nail, no more bone than necessary is removed in order to accommodate an intramedullary nail's width and the shallow angle.

After the entry hole 50 is properly reamed, the remaining portion of the implantation procedure is substantially similar to one of the known techniques for implanting an intramedullary nail in an elongated bone. For instance, a reamer may be advanced through the interior of bone 5 along a guide rod in preparation for the nail. After being properly reamed, a retrograde humeral nail 48 is positioned across fracture 6 in a conventional manner and secured in place utilizing standard locking screws 49, of a type known in the art.

Referring now to FIG. 8, the geometrical relationships between the various holes made in the bone and the various axes of the pin placement guide are illustrated to better show the advantageous features of the present invention. As discussed earlier, pilot axis 22 is arranged in relation to guide axis 32 so that the two axes intersect at a point 33 which is located at about the outer surface of the bone when the device is clamped thereto as described earlier. In the case of a retrograde humeral nail, it has been found that the procedure works better when the pilot hole 51 is actually of a larger diameter than guide hole 52. Realizing that the main purpose of pilot hole 51 is to enable the boring tip of guide pin 44 to better engage bone 5 at an interior point 55 that will better facilitate the boring of guide hole 52. With the guide hole 52 bored at the desired angle alpha with respect to bone axis 14, a reamer of a larger diameter is then advanced along guide axis 32 to enlarge guide hole 52 into an entry hole 50. As described earlier, entry hole 50 is preferably on the order of about 1 millimeter larger than the nail to be inserted into the bone. And, the axis of the entry hole is preferably made at a shallower angle than the guide axis by exploiting the limited maneuverability of the guide pin when the pin placement guide has been removed. In the case of a retrograde humeral nail, pilot hole 51 is preferably on the order of about 3.6 millimeters in diameter, the guide hole is preferably on the order of about 2.4 millimeters in diameter and the entry hole is on the order of about 10 millimeters in diameter.

By utilizing the technique of the present invention, no more bone than necessary is removed in order to facilitate the insertion of the intramedullary nail. Furthermore, the entry opening is made in such a way that minimizes the risk of cracking or otherwise damaging the bone, which sometimes occurs in the prior art. Those skilled in the art should appreciate that the above description is intended for illustrative purposes only and is not intended to limit the scope of the present invention in any way. For instance, while the invention has been illustrated for use in implanting a retrograde humeral nail, the present invention also finds potential application in the implantation of an intramedullary nail in virtually any elongated bone. Thus the scope of the present invention should be determined solely in terms of the claims as set forth below.

We claim:

1. A pin placement guide for use in making an entry hole to implant an intramedullary nail across a fracture in an elongated bone, the pin placement guide comprising:

a base having a bone contact surface defining a longitudinal axis;

a guide portion attached to said base, and having a guide bore with a guide axis extending through said guide portion and said bone contact surface of said base; and said guide axis being at a an invariably fixed angle of less than twenty degrees with respect to said longitudinal axis.

2. The pin placement guide of claim 1 wherein said base includes a pilot bore with a pilot axis extending through said base and said bone contact surface; and said pilot bore and said guide bore being sized and arranged such that a tip of a guide pin inserted through said guide bore along said guide axis will enter a pilot hole in said elongated bone made by a drilling device inserted through said pilot bore along said pilot axis.

3. The pin placement guide of claim 2 further comprising means for clamping said base to said elongated bone.

4. The pin placement guide of claim 1 further comprising a handle that includes a pilot bore defining a pilot axis extending through said handle and said bone contact surface of said base; and said pilot axis intersects said guide axis adjacent said bone contact surface.

5. The pin placement guide of claim 2 wherein said longitudinal axis, said guide axis and said pilot axis are coplanar; and said pilot axis is at an angle greater than forty-five degrees with respect to said longitudinal axis.

6. The pin placement guide of claim 1 wherein said guide axis is at a fixed angle of between 5 and 15 degrees with respect to said longitudinal axis.

7. The pin placement guide of claim 1 wherein said guide axis is at a fixed angle of about ten degrees with respect to said longitudinal axis.

8. The pin placement guide of claim 7 wherein said pilot axis is at a fixed angle of about sixty degrees with respect to said longitudinal axis.

9. The pin placement guide of claim 2 wherein said pilot bore has a diameter larger than said guide bore.

10. A pin placement guide for use in making an entry hole to implant an intramedullary nail across a fracture in an elongated bone the pin placement guide comprising:

a base having a bone contact surface defining a said longitudinal axis;

a guide portion attached to said base, and having a guide bore with a guide axis extending through said guide portion and said bone contact surface of said base; and said guide axis being at an angle of greater than zero but less than twenty degrees with respect to said longitudinal axis;

a handle that includes a pilot bore with a pilot axis extending through said handle and said bone contact surface of said base; and said pilot bore and said guide bore being sized and arranged such that a tip of a guide pin inserted through said guide bore along said guide axis will enter a pilot hole in said elongated bone made by a drilling device inserted through said pilot bore along said pilot axis.

11. The pin placement guide of claim 10 wherein said pilot axis intersects said guide axis adjacent said bone contact surface.

12. The pin placement guide of claim 11 wherein said longitudinal axis, said guide axis and said pilot axis are coplanar; and said pilot axis is at an angle greater than forty-five degrees with respect to said longitudinal axis.

13. The pin placement guide of claim 12 wherein said pilot bore has a diameter larger than said guide bore.

14. The pin placement guide of claim 13 further comprising a clamp for clamping said base to said elongated bone.

15. The pin placement guide of claim 14 wherein said guide axis is at a fixed angle of about ten degrees with respect to said longitudinal axis.

16. The pin placement guide of claims 15 wherein said pilot axis is at a fixed angle of about sixty degrees with respect to said longitudinal axis.

17. A pin placement guide for use in making an entry hole to implant an intramedullary nail across a fracture in an elongated bone, the pin placement guide comprising:

a base having a bone contact surface defining a longitudinal axis;

a guide portion attached to said bases and having a guide bore with a guide axis extending through said guide portion and said bone contact surface of said base; and said guide axis being at a fixed angle of greater than zero but less than twenty degrees with respect to said longitudinal axis; and said pin placement guide being machined from a single solid piece of a metallic alloy.

18. The pin placement guide of claim 17 further comprising an integral handle that includes a pilot bore with a pilot axis extending through said handle and said bone contact surface of said base;

said pilot bore and said guide bore being sized and arranged such that a tip of a guide pin inserted through said guide bore along said guide axis will enter a pilot hole in said elongated bone made by a drilling device inserted through said pilot bore along said pilot axis.

19. The pin placement guide of claim 18 wherein said pilot bore has a diameter larger than said guide bore.

20. The pin placement guide of claim 19 wherein said longitudinal axis, said guide axis and said pilot axis are coplanar; and said pilot axis is at an angle greater than forty-five degrees with respect to said longitudinal axis.

* * * * *